(12) United States Patent
Keizer

(10) Patent No.: US 7,319,899 B2
(45) Date of Patent: Jan. 15, 2008

(54) SENSING TECHNIQUES FOR IMPLANTABLE MEDICAL DEVICES

(75) Inventor: Diederick M. Keizer, Elst (NL)

(73) Assignee: Medtronic, Inc., Minneapolis, MN (US)

( * ) Notice: Subject to any disclaimer, the term of this patent is extended or adjusted under 35 U.S.C. 154(b) by 370 days.

(21) Appl. No.: 10/422,080

(22) Filed: Apr. 23, 2003

(65) Prior Publication Data

US 2004/0215265 A1 Oct. 28, 2004

(51) Int. Cl.
*A61N 1/00* (2006.01)
(52) U.S. Cl. .......................... 607/19; 607/18
(58) Field of Classification Search ............ 607/19–20, 607/17; 600/523; 340/575
See application file for complete search history.

(56) References Cited

U.S. PATENT DOCUMENTS

| | | | |
|---|---|---|---|
| 4,771,780 A | 9/1988 | Sholder | |
| 4,846,195 A | 7/1989 | Alt | |
| 5,040,536 A | 8/1991 | Riff | |
| 5,187,657 A * | 2/1993 | Forbes | 600/513 |
| 5,233,984 A | 8/1993 | Thompson | |
| 5,476,483 A | 12/1995 | Bornzin et al. | |
| 5,485,851 A * | 1/1996 | Erickson | 600/529 |
| 5,518,001 A * | 5/1996 | Snell | 600/510 |
| 5,622,428 A | 4/1997 | Bonnet | |
| 5,630,834 A * | 5/1997 | Bardy | 607/5 |
| 5,766,228 A * | 6/1998 | Bonnet et al. | 607/16 |
| 5,785,660 A * | 7/1998 | van Lake et al. | 600/523 |
| 5,876,353 A * | 3/1999 | Riff | 600/547 |
| 6,049,735 A * | 4/2000 | Hartley et al. | 607/9 |
| 6,128,534 A | 10/2000 | Park et al. | |
| 6,161,041 A * | 12/2000 | Stoop et al. | 607/14 |
| 6,259,948 B1 | 7/2001 | Florio et al. | |
| 6,920,229 B2 * | 7/2005 | Boesen | 381/380 |
| 2002/0193839 A1 * | 12/2002 | Cho et al. | 607/17 |
| 2004/0006375 A1 * | 1/2004 | Poezevera | 607/17 |
| 2004/0111041 A1 * | 6/2004 | Ni et al. | 600/529 |

* cited by examiner

*Primary Examiner*—Carl Layno
*Assistant Examiner*—Brian T. Gedeon
(74) *Attorney, Agent, or Firm*—Daniel G. Chapik

(57) ABSTRACT

The invention is directed to sensing techniques that can be executed by an implantable medical device (IMD). The sensing techniques exploit the fact that useful information can be sensed during the periods where the sympathetic and vagal tone balance changes in a patient's nervous system. This balance generally changes when a patient is falling asleep or waking up from sleep. In accordance with the invention, sensed information is recorded specifically during the times where a patient is either falling asleep or waking up. The IMD can be designed to sense or identify when a patient is falling asleep or waking up, and can record the useful sensed information specifically during those times.

14 Claims, 5 Drawing Sheets

SENSING TECHNIQUES FOR IMPLANTABLE MEDICAL DEVICES

FIELD OF THE INVENTION

The invention relates to implantable medical devices (IMDs), and more particularly to IMDs that have sensing or monitoring capabilities.

BACKGROUND OF THE INVENTION

A wide variety of implantable medical devices (IMDs) have been developed in order to monitor patient conditions and deliver therapy to the patient. An IMD typically includes a hermetically sealed housing coupled to one or more leads that are surgically implanted inside a patient for short or long term therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. Telemetry can be used to communicate sensed information from the IMD to an external medical device so that analysis can be performed. Also, in some cases, the sensed information may be used directly by the IMD to adjust or control the therapy that is delivered to the patent.

One common example of an IMD is a pacemaker. A pacemaker typically includes a pacemaker device and one or more pacing and sensing leads for delivery of pacing pulses to a patient's heart and sensing of heart conditions. Another example of an IMD is a combination pacemaker-cardioverter-defibrillator. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

IMDs often sense and record electrograms or other biomedical information associated with a patient. Electrograms refer to signals which represent recorded changes in electric potential of the patient. Examples of electrograms include electrocardiograms, i.e., recorded electrical potentials associated with a patient's heart, and electroencephalograms, i.e., recorded electrical potentials associated with a patient's brain. Other more specific examples of electrograms include atrial electrograms, coronary sinus (CS) electrograms, esophageal electrograms, high right atrial (HRA) electrograms, His bundle electrograms, intra-atrial electrograms, intracardiac electrograms, left and right ventricular electrograms, right ventricular apical electrograms, sinus node electrograms, and the like.

IMDs typically sense and store information in a continuous fashion. In many cases, the stored information is averaged over whole or half days. For example, measurements of a patient's heart rate may be continuously measured and averaged. Similarly, measurements of amplitudes or frequency associated with specific features of electrocardiograms may be accumulated in a continuous fashion. However, continuous monitoring techniques can limit the diagnostic usefulness of the measured information.

BRIEF SUMMARY OF THE INVENTION

In general, the invention is directed to sensing techniques that can be executed by an implantable medical device (IMD). The sensing techniques recognize that sensed information is particularly useful if collected during the period where the sympathetic and vagal tone balance changes in a patient's nervous system. In particular, during periods where the sympathetic and vagal tone balance changes in a patient's nervous system, the most striking effects in the patient's biological system can be observed. The balance between sympathetic and vagal tone generally changes during periods when the patient falls asleep or wakes up from sleep. Therefore, in accordance with the invention, sensed information is recorded specifically during the times where a patient is either falling asleep or waking up.

In one embodiment, the invention provides an implantable medical device comprising a sensor implanted within a patient, a controller coupled to the sensor, and a memory coupled to the controller. The controller identifies that a patient is going to sleep and records in the memory information sensed by the sensor for a time interval associated with the patient going to sleep.

In another embodiment, the invention provides an implantable medical device comprising a controller, a memory coupled to the controller, a heart sensor coupled to the controller, a respiratory sensor coupled to the controller, and a position sensor coupled to the controller. The controller identifies that a patient is going to sleep based on information received from the respective sensors and records in the memory, information sensed by one or more of the sensors for a time interval associated with the patient going to sleep.

In another embodiment, the invention provides a method comprising detecting that a patient is going to sleep, and recording information sensed by an implantable medical device for a time interval associated with the patient going to sleep.

In another embodiment, the invention provides a method comprising detecting that a patient is waking up from sleep, and recording information sensed by an implantable medical device for a time interval associated with the patient waking up.

In another embodiment, the invention provides an implantable medical device comprising means for detecting that a patient is going to sleep, and means for recording information sensed by the implantable medical device for a time interval associated with the patient going to sleep.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The invention is directed to sensing techniques that can be executed by an implantable medical device (IMD). The sensing techniques exploit the fact that useful information can be sensed during the periods when the sympathetic and vagal tone balance changes in a patient's nervous system. This balance typically changes when a patient is falling asleep or waking up from sleep. Therefore, in accordance with the invention, sensed information is recorded specifically during the times where a patient is either falling asleep or waking up. The IMD can be designed to sense or identify when a patient is falling asleep or waking up, and can record the useful sensed information specifically during those times.

Figure 1:
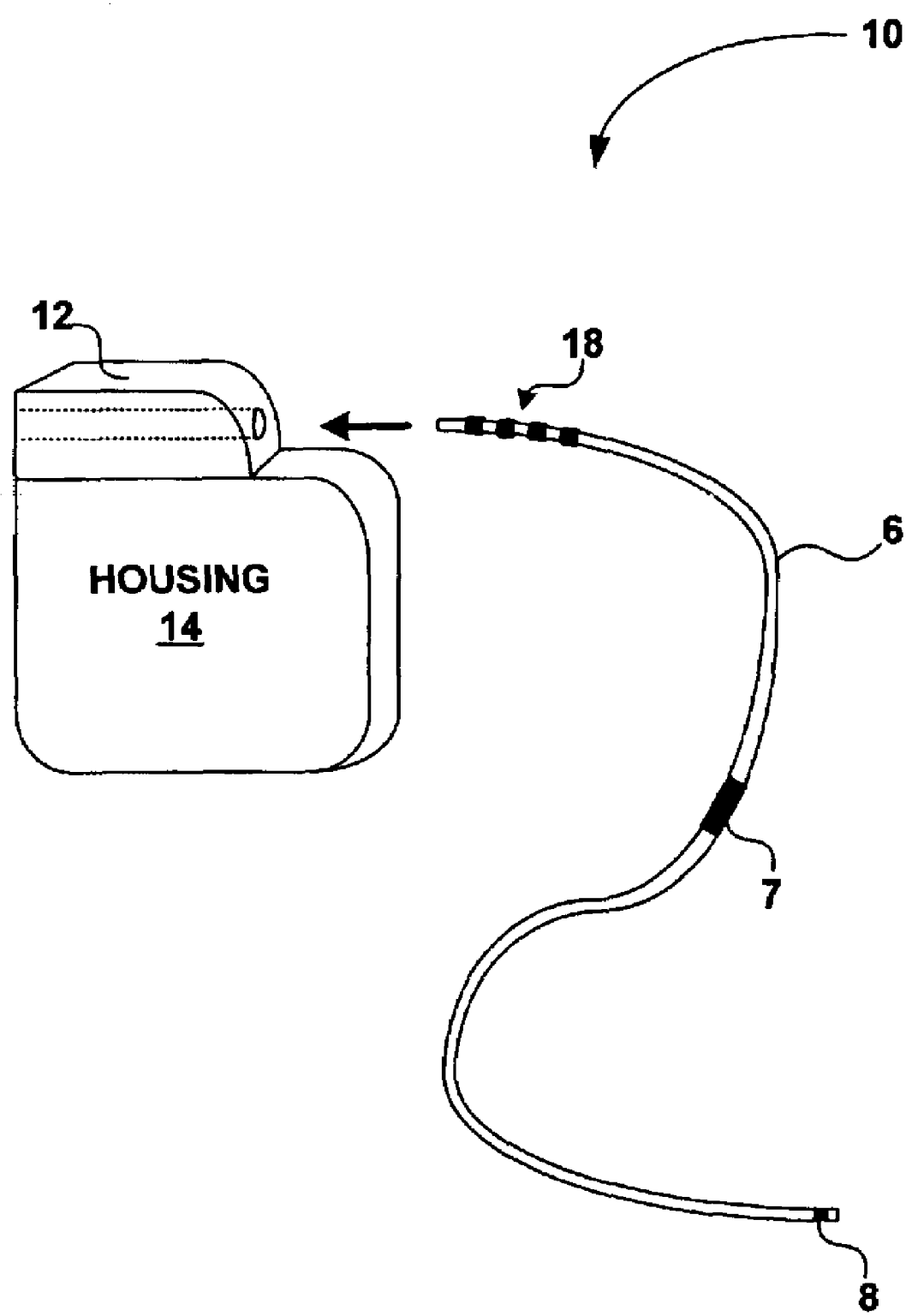
FIG. 1 is a schematic view of an IMD comprising a hermetically sealed housing coupled to implantable leads to position sensor elements within a patient.

FIG. 1 is a schematic view of an IMD 10 comprising a hermetically sealed housing 14 and one or more implantable leads 6. Lead 6 may position one or more sensor elements 7, 8 within a patient to sense various conditions within the patient. Sensor elements 7, 8 may comprise electrodes used to sense electrical potentials within a patient, or may comprise other types of sensors as described in greater detail below. If one or more of sensor elements 7, 8 comprise electrodes, the electrodes may also be used for delivering stimulation pulses to an implanted location within a patient.

For example, sensor element 8 may comprise a heart rate sensor and sensor element 7 may comprise a respiratory sensor. In addition, IMD 10 may contain a position sensor that is used to sense whether a patient is lying down or standing up. As described in greater detail below, these or other types of sensor elements may be used to identify when a patient is going to sleep or waking up. Recording sensed conditions specifically during time intervals associated with changes in the balance between sympathetic and vagal tone can improve the diagnostic value of the recorded information. Also, memory and power requirements may be reduced relative to systems that record sensed conditions continuously.

Implantable lead 6 may include any number of additional sensor elements or electrodes distributed along the length of lead. Electrodes (if desired) can be made from an electrically conductive, biocompatible material such as elgiloy, platinum, platinum-iridium, platinum-iridium oxide, sintered platinum powder or other residue product after combustion with some high heat source, platinum coated with titanium-nitride, pyrolytic carbon, or the like.

Sensor elements 7, 8 can be electrically coupled to one or more conductive filars that extend along the body of lead 6, e.g., in a coiled construction. For example, each of sensor elements 7, 8 may be electrically coupled to one of electrical interfaces 18 via the filars that extend along the body of lead 6. Although a single lead 6 is shown for purposes of illustration, any number of leads may be used in IMD 10, and thus coupled to connector module 12 of housing 14.

IMD 10 comprise any device capable of recording sensed information of a patient. For example, IMD 10 may take the form of an implantable cardiac pacemaker, a combination pacemaker-cardioverter-defibrillator, or the like. The invention, however, is not limited for use with cardiac pacing, but may find wide applicability with any IMD that has sensing capabilities.

Figure 2:
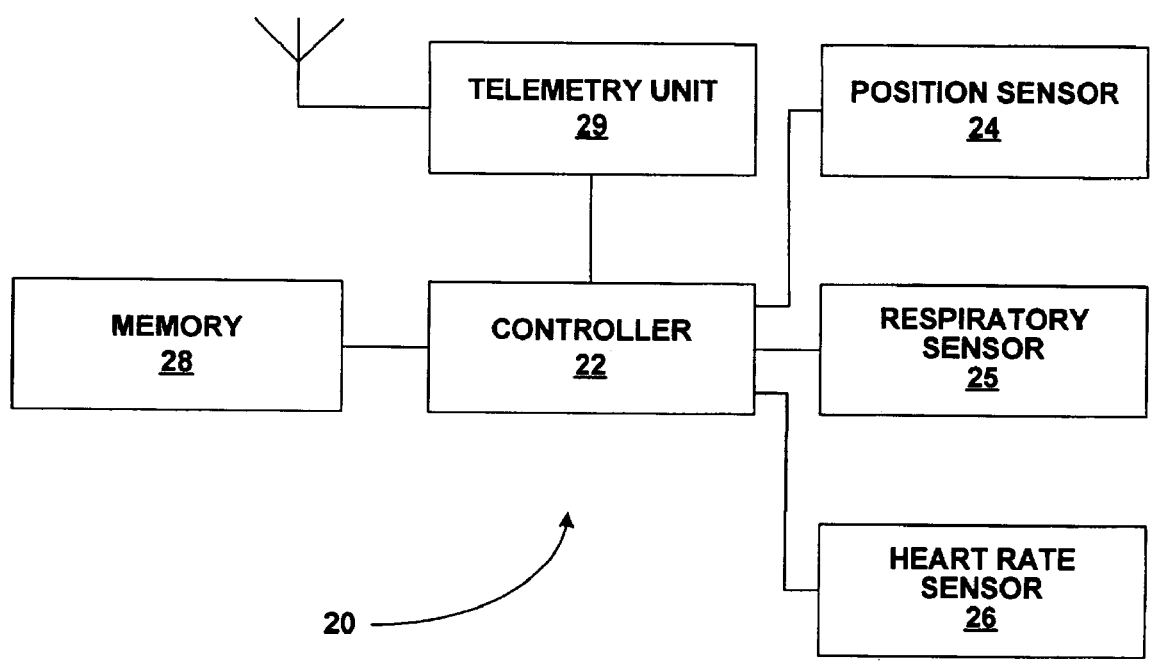
FIG. 2 is a block diagram of an exemplary IMD in accordance with an embodiment of the invention.

FIG. 2 is a block diagram of an exemplary IMD 20 in accordance with an embodiment of the invention. IMD 20 may correspond to IMD 10 of FIG. 1. IMD 20 includes a position sensor 24, a respiratory sensor 25 and a heart sensor 26. The sensors 24, 25, 26 are coupled to a controller 22. A memory 28 for storing information sensed by one or more of sensors 24, 25, 26 is also coupled to controller 22. In addition, IMD 20 may include a telemetry unit 29 coupled to controller 22, e.g., to facilitate communication between IMD 10 and another device such as an external programmer.

Controller 22 receives sensed information from position sensor 24, respiratory sensor 25 and heart sensor 26, and based on the information received from sensors 24, 25, 26, controller 22 identifies when a patient is going to sleep or waking up. For example, controller 22 may execute an algorithm that identifies that a patient is going to sleep or waking up when specific conditions are sensed by one or more of sensors 24, 25, 26. Upon identifying that a patient is going to sleep, controller 22 stores sensed information in memory 28. Similarly, upon identifying that a patient is waking up, controller 22 stores sensed information in memory 28. In this manner, sensed information is accumulated during periods where the balance changes between the sympathetic and parasympathetic nervous systems. Hence, more useful detail of the patient's biology may be preserved in the information. In some cases, the sensed information is stored for a fixed time period, and this fixed time period may be a programmable value that can be selected by a physician.

Position sensor 24 may comprise a sensor contained within the housing of the IMD, e.g., within housing 14 (FIG. 1). Position sensor 24 may comprise any sensor element capable of identifying positioning relative to the ground, i.e., the surface of the earth. In one example, position sensor 24 may comprise a capsule-like housing that contains a mercury ball and various electrodes. The mercury ball can move in the capsule-like housing in response to the earth's gravitational forces. Movement of the mercury ball can cause the mercury ball to come into contact with one or more electrodes. Positioning of sensor 24, and thus positioning of IMD 20 can be determined based on which electrodes are in contact with the mercury ball inside the capsule-like housing. U.S. Pat. No. 4,846,195 describes one example of a position sensor that may be used, and is incorporated herein by reference in its entirety.

Respiratory sensor 25 may comprise any sensor element capable of identifying one or more factors associated with a patients breathing, such as the patient's respiratory rate. For example, respiratory sensor 25 may obtain impedance-based measurements at locations within a patient's thoracic cavity. Such impedance-based measurements can be used to identify when a patient is breathing in or out, and can therefore be used to determine the respiratory rate. Alternatively, electrical in the activity thoracic cavity may be measured to determine respiratory rate or respiratory activity.

Heart sensor 26 may comprise one or more electrodes positioned at a location in the patient's heart, e.g., via implanted leads. Heart sensor 26 may sense depolarizations of the heart, and can be used to sense electrocardiograms, heart rate, or the like. If desired, a number of heart sensors may be used, e.g., in conjunction with multi-chamber pacing techniques. The same signals may also be obtained by using leadless system like the such as the MDT Reveal system, commercially available from Medtronic of Minneapolis, Minn. In that case, the sensing electrodes are on the medical device housing are able to sense cardiac activity.

Controller 22 may comprise any of a wide variety of hardware or software configurations capable of executing algorithms to detect when a patient is falling asleep or waking up. Example hardware implementations of controller 22 include implementations within an application specific integrated circuit (ASIC), a field programmable gate array (FPGA), a programmable logic device, specifically designed hardware components, one or more processors, or any combination thereof. If implemented in software, a computer readable medium, such as memory 28, may store computer readable instructions, e.g., program code, that can be executed by controller 22 to carry out one of more of the techniques described herein. For example, memory 28 may comprise random access memory (RAM), read-only memory (ROM), non-volatile random access memory (NVRAM), electrically erasable programmable read-only memory (EEPROM), flash memory, or the like.

Telemetry unit 29 may comprise any unit capable of facilitating wireless data transfer between IMD 20 and a programmer or other external medical device. For example, telemetry unit 29 may send and receive radio frequency (RF) signals, infrared (IR) frequency signals, or other electromagnetic signals. Any of a variety of modulation techniques may be used to modulate data on a respective electromagnetic carrier wave. Alternatively, telemetry unit 29 may use sound waves for communicating data, or may use the patient's tissue as the transmission medium for communicating with a programmer positioned on the patients skin. In any event, telemetry unit 29 facilitates wireless data transfer between IMD 20 and a programmer or other external medical device.

In accordance with the invention, controller 22 receives sensed information from position sensor 24, respiratory sensor 25 and heart sensor 26, and based on the information received from sensors 24, 25, 26, identifies when a patient is going to sleep or waking up. Upon identifying that a patient is going to sleep, controller 22 stores sensed information in memory 28. Similarly, upon identifying that a patient is waking up, controller 22 stores sensed information in memory 28.

For example, controller 22 may receive information from position sensor 24 indicating that a patient is lying down, which would tend to indicate the possibility that the patient is falling asleep. Controller 22 may also receive information from respiratory sensor 25 indicating the patient's respiratory rate. The measured respiratory rate may be compared to a respiratory rate threshold, which may be fixed or may be programmed into IMD 20 via use of telemetry unit 29. Measured respiratory rates below the respiratory rate threshold would tend to indicate that the patient is falling asleep. The respiratory rate threshold used for any given patient may be selected by a physician based on the patient's breathing habits or normal breathing rate. Alternatively, the time rate of change of the patient's respiration may be used to identify when the patient is falling asleep.

Controller 22 may also receive information from heart sensor 26 indicating the patient's heart rate. The measured heart rate may be compared to a heart rate threshold, which may be fixed or may be programmed into IMD 20 via use of telemetry unit 29. Measured heart rates below the heart rate threshold would tend to indicate that the patient is falling asleep. The heart rate threshold used for any given patient may be selected by a physician based on the patient's normal heart rate. Alternatively, the time rate of change of the patient's heart rate may be used to identify when the patient is falling asleep.

In one example, controller 22 detects that a patient is falling asleep upon identifying from sensors 24, 25, 26 at least two of the following: 1) a reduction in heart rate below the heart rate threshold, 2) a reduction in respiratory rate below the respiratory rate threshold, or 3) an indication that the patient is lying down based on positioning of position sensor 24. Upon identifying at least two of these occurrences, controller 22 may store sensed information, such as sensed electrocardiograms, sensed heart rates, sensed respiratory rates, or the like, in memory 28. Numerous other sensed information, including information sensed from other sensors (not shown) may also be stored in memory 28. Importantly, however, sensed information is stored specifically when controller 22 determines that the patient is falling asleep.

In another example, a first trigger from one or more sensors provides an indication that the patient is going to sleep. The first trigger can start the recording of sensed information. In that case, the recording continues for a certain time, and during this time, a confirmation of a second trigger should be received in order to keep the information. In other words, detecting that the patient is going to sleep includes identifying a first trigger of sensed information to initiate the recording and identifying a second trigger of sensed information to verify that the patient is going to sleep following the initiation of the recording.

If no conformation, i.e., no second trigger is obtained, the stored information is deleted and the cycle starts again. However, if the second trigger is obtained following the initiation of recording, the recorded information is stored and then communicated to a physician. The sensed events that cause the first and second triggers are subject to a wide variety of events such as described herein.

The recording of sensed information into memory 28 may occur for a fixed or defined period, which may also be programmed into IMD 20 via use of telemetry unit 29. For example, if the patient generally takes a long time to fall asleep, the physician may choose to define a larger time interval for recording of sensed information into memory 28 following the identification that the patient is falling asleep. Similarly, if the patient typically falls asleep very quickly, the physician may choose to define a smaller time interval for recording of sensed information into memory 28 following the identification that the patient is falling asleep.

In some cases, controller 22 may dynamically establish the time interval for recording of sensed information into memory 28. For example, once controller 22 has identified that the patient is falling asleep, and invoked recording of sensed information into memory 28, controller 22 may subsequently detect that the patient has fallen asleep. Once the patient is asleep (as opposed to falling asleep), controller 22 can terminate the recording of sensed information. In order to identify that the patient is asleep (as opposed to falling asleep), controller 22 may identify a heart rate below another heart rate threshold, e.g., lower than the heart rate threshold used to identify that the patent was falling asleep. Alternatively or additionally, controller 22 may identify that the patient is asleep (as opposed to falling asleep), by identifying a respiratory rate below another respiratory rate threshold, e.g., lower than the respiratory rate threshold used to identify that the patent was falling asleep.

Controller 22 may operate similarly in detecting that a patient is waking up. In particular, controller 22 receives sensed information from position sensor 24, respiratory sensor 25 and heart sensor 26, and based on the information received from sensors 24, 25, 26, identifies when a patient waking up. Upon identifying that the patient is waking up, controller 22 may store sensed information, such as sensed electrocardiograms, sensed heart rates, sensed respiratory rates, or the like, in memory 28. Again, numerous other sensed information, including information sensed from other sensors (not shown) may also be stored in memory 28. Importantly however, in this case, sensed information is stored specifically when controller 22 determines that the patient is waking up.

For example, controller 22 may detect that a patient is waking up by identifying an increase in heart rate above a heart rate threshold, and/or identifying an increase in respiratory rate above a respiratory rate threshold. Alternatively, changes in the heart rate or respiratory rate may be used by controller to identify when the patient is waking up or falling asleep, e.g., by comparing the rate changes to rate change thresholds. The thresholds defined for waking up may be different than the thresholds defined to identify that the patient is falling asleep, or asleep. Any or all of the thresholds may be programmable such that a physician can adapt IMD 20 by programming the thresholds to correspond to a specific patient's specific sleep habits. An indication from position sensor 24 that the patient is standing up or not lying down, would generally indicate that the patient is awake.

Like during the falling asleep period, during the waking up period, the recording of sensed information into memory 28 may occur for a fixed or defined time interval, which may also be programmed into IMD 20 via use of telemetry unit 29. Alternatively, controller 22 may dynamically establish the time interval for recording of sensed information into memory 28 during the wake up period. For example, once controller 22 has identified that the patient is waking up, and initiated recording of sensed information into memory 28, controller 22 may subsequently detect that the patient is awake. Once the patient is awake (as opposed to waking up), controller 22 can terminate the recording of sensed information. In order to identify that the patient is awake (as opposed to waking up), controller 22 may identify a heart rate above some threshold, or controller 22 may identify a respiratory rate above some respiratory rate threshold. Also, controller 22 may identify that the patient is awake (as opposed to waking up), once position sensor 24 indicates that the patient is not lying down.

In other embodiments, IMD 20 may include a patient activator. For example, a patient may be able to activate a button, or may send telemetry signals from a programmer to telemetry unit 29 to indicate that the patient is going to sleep or has woken up. IMD 20 can be configured to respond to such patient activation. When the patient tells IMD 20 that he or she is going to sleep, e.g., via use of a programmer that communicates with telemetry unit 29, IMD 20 may record sensed information for the falling asleep period as described herein. Also, IMD 20 may implement timers to invoke or terminate recording at an interval relative to patient communication indicating an intent to go to sleep.

Examples of the type of sensed information that may be recorded during the periods of falling asleep and waking up include: QT interval changes during such periods, QT interval dispersions, heart rate, respiratory rate, heart rate variability, respiratory rate variability, T-wave variations, onset of atrial fibrillations, onset of ischemia, interval timing of any specific features of the electrogram, or any other information that can be sensed or obtained through the use of sensors.

Figure 3:
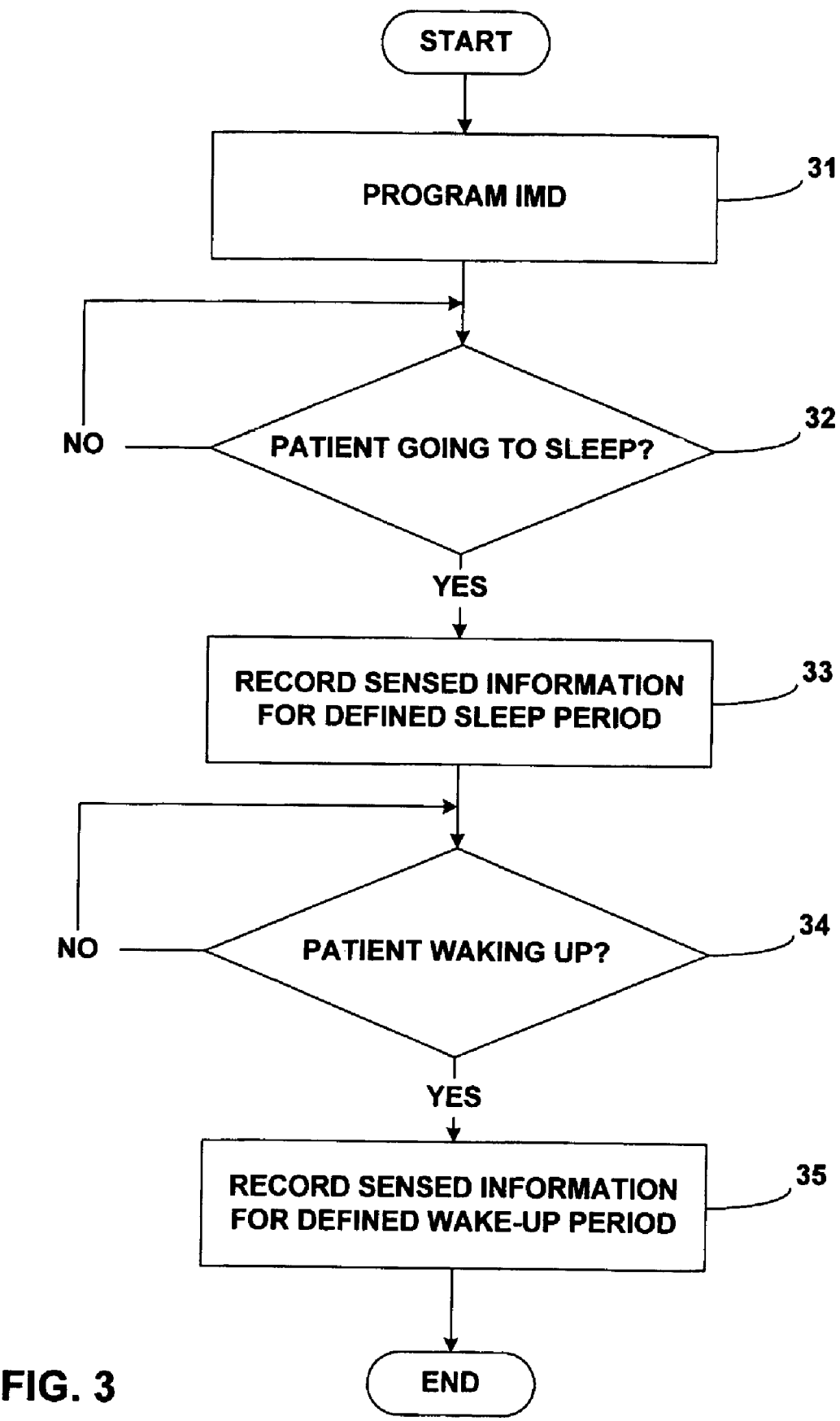
FIG. 3 is a flow diagram illustrating a method for selectively recording sensed information according to an embodiment of the invention.

FIG. 3 is a flow diagram according to an embodiment of the invention. As shown, in FIG. 3, a physician programs IMD 20 (31), e.g., via telemetry. In particular, the physician may program the various thresholds for heart rate and respiratory rate that define when the patient is falling asleep (for invoking recording of sensed conditions during the falling asleep period), when the patient is asleep (for termination of recording during the falling asleep period), when the patient is waking up (for invoking recording of sensed conditions during the waking up period), and when the patient is awake (for termination of recording during the falling asleep period).

Additionally or alternatively, the physician may program time intervals into IMD 20 to specifically define the amount of time for recording of sensed conditions following identification that the patient is falling asleep or waking up. These time intervals may be selected differently based on the patients sleep habits. If the patient generally takes a long time to fall asleep, the amount of time for recording of sensed conditions can be made larger, and if the patient generally falls asleep very quickly, the amount of time for recording of sensed conditions can be made smaller.

Controller 22 identifies when a patient is going to sleep (32), and upon identifying that the patient is going to sleep (yes branch of 32), records in memory 28 sensed information for a defined sleep period (33). Again, the defined sleep period may be selected by the physician and programmed into controller 22 via communication between telemetry unit 29 and an external programmer.

In one example, controller 22 detects that a patient is falling asleep (32) upon identifying from sensors 24, 25, 26 at least two of the following: 1) a reduction in heart rate below the heart rate threshold, 2) a reduction in respiratory rate below the respiratory rate threshold, or 3) an indication that the patient is lying down based on positioning of position sensor 24. Again, numerous other sensed information, including information sensed from other sensors may also be stored in memory 28. Importantly, however, sensed information is stored specifically when controller 22 determines that the patient is falling asleep (yes branch of 32).

Controller 22 then identifies when a patient is waking up (34), and upon identifying that the patient is waking up (yes branch of 34), records in memory 28 sensed information for a defined wake up period (35). Again the defined wake up period may be selected by the physician and programmed into controller 22 via communication between telemetry unit 29 and an external programmer.

In one example, controller 22 detects that a patient is waking up (34) by identifying an increase in heart rate above a heart rate threshold, and/or identifying an increase in respiratory rate above a respiratory rate threshold. These thresholds may be programmed or may be fixed. Moreover, the thresholds used to determine when the patient is waking up are generally different than the thresholds used to determine when the patient is falling asleep, although the invention is not necessarily limited in that respect.

In general, sensed information is recorded during the periods where the sympathetic and vagal tone balance changes in a patient's nervous system. This balance changes when a patient is falling asleep or waking up from sleep. Accordingly, in accordance with the invention, controller 22 stores sensed information in memory 28 specifically during the times where a patient is either falling asleep or waking up. In this manner, the diagnostic value of the stored information can be improved. In addition, such techniques may reduce memory requirements in IMD 20 and prolong battery life since recording does not occur continuously.

Figure 4:
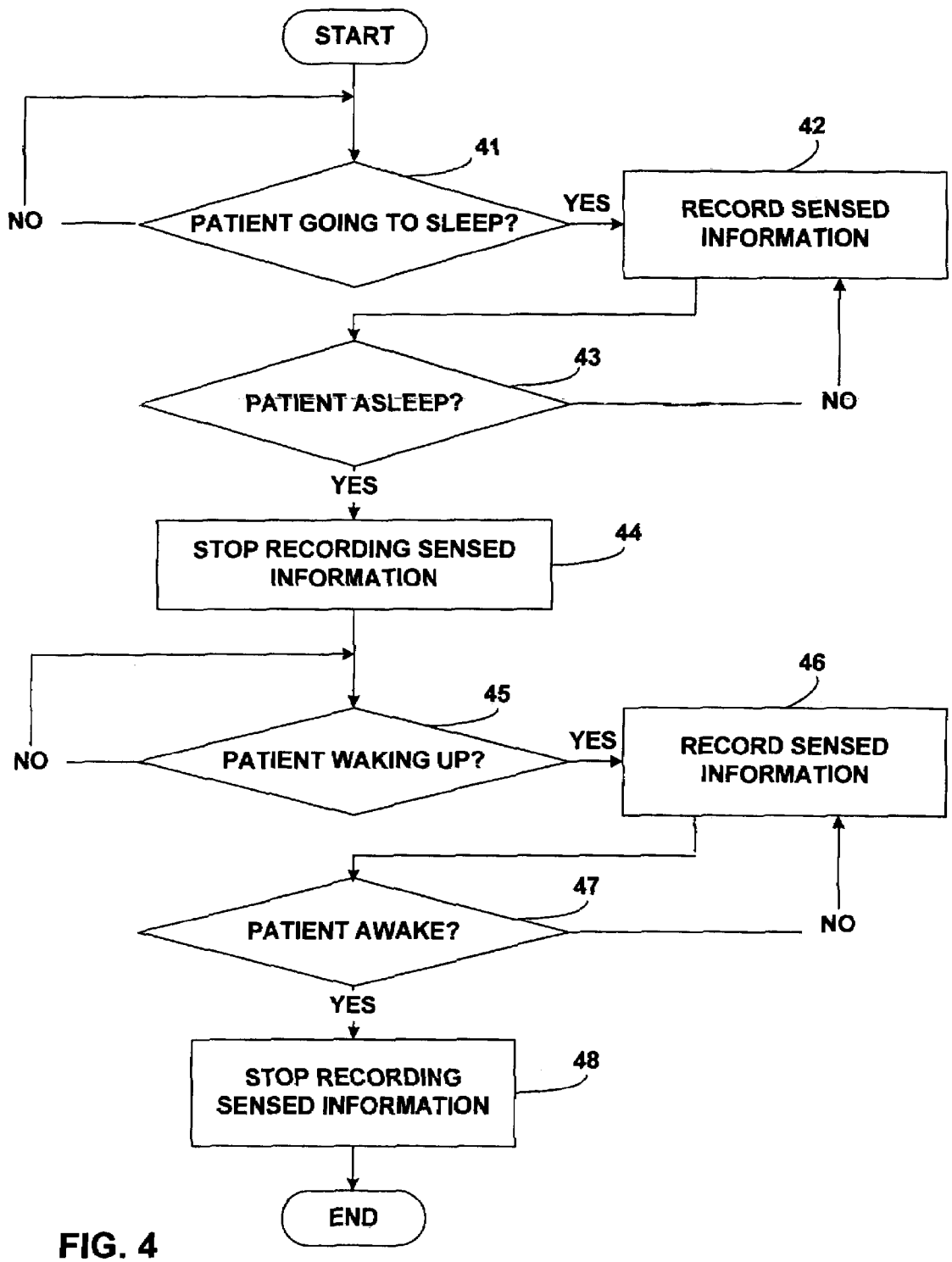
FIG. 4 is another flow diagram illustrating another method for selectively recording sensed information according to an embodiment of the invention in which the recording periods are dynamically determined by the IMD.

FIG. 4 is another flow diagram according to an embodiment of the invention in which the recording periods are dynamically determined by IMD 20. As shown in FIG. 4, controller 22 identifies when a patient is going to sleep (41), and upon identifying that the patient is going to sleep (yes branch of 41), records sensed information in memory 28. In this example, sensed information is stored in memory 28 until controller 22 identifies that the patient is asleep (43).

When controller 22 identifies that the patient is asleep (yes branch of 43), it stops recording the sensed information in memory 28 (44). In other words, controller 22 first identifies that a patient is falling asleep (yes branch of 41), and records sensed information in memory 28 (42) until controller 22 subsequently identifies that the patient is asleep (yes branch of 43).

Controller 22 next identifies when a patient is going waking up (45), and upon identifying that the patient is waking up (yes branch of 45), records sensed information in memory 28 (46). In particular, the sensed information is stored in memory 28 until controller 22 identifies that the patient is awake (47). When controller 22 identifies that the patient is awake (yes branch of 47), it stops recording the sensed information in memory 28 (48). In other words, controller 22 identifies that a patient is waking up (yes branch of 47), and records sensed information in memory 28 (46) until controller 22 subsequently identifies that the patient is awake (yes branch of 47).

Controller 22 may implement any of a wide variety of techniques for identifying when a patient is going to sleep (41), when the patient is asleep (43), when the patient is waking up (45), and when the patient is awake (47). For example, different heart rate thresholds and respiratory rate thresholds may be defined for each of these events. Heart sensor 26 and respiratory sensor 25 can measure the patient's heart rate and respiratory rate respectively. Controller 22 can receive the measured heart rate and respiratory rate and can compare the measured rate the appropriate thresholds to identify when a patient is going to sleep (41), when the patient is asleep (43), when the patient is waking up (45), and when the patient is awake (47).

Additionally, output from position sensor 24 may be used by controller 22 to identify whether a patient is lying down (indicating that the patient may be falling asleep) or standing up (indicating that the patient is awake). Also, patient triggering may be used in which the patient telemetrically communicates with an IMD to indicate that he or she is going to sleep, or has awaken. These or other techniques may be used to allow sensed information to be recorded and accumulated at the specific time intervals associated with falling asleep and waking up, but not during other time intervals when the patient is asleep or awake. Again, the recording of sensed information during the periods where the sympathetic and vagal tone balance changes in a patient's nervous system can be particularly useful for diagnostic purposes.

After accumulation for one or more days, the recorded information may be telemetrically communicated to an external programmer or other diagnostic device for evaluation or analysis by a physician. In other words, after sufficient sensed information has been stored in memory 28, controller 22 may access the information and provide it to telemetry unit 29 for telemetric communication to an external device. In this manner, a physician may access the specific information collected during the periods where the sympathetic and vagal tone balance changes in a patient's nervous system, and may analyze or otherwise use the information for diagnostic purposes. In some cases, the external device is connected to a network, such as the internet, and the physician can access the telemetrically communicated information via the network.

Figure 5:
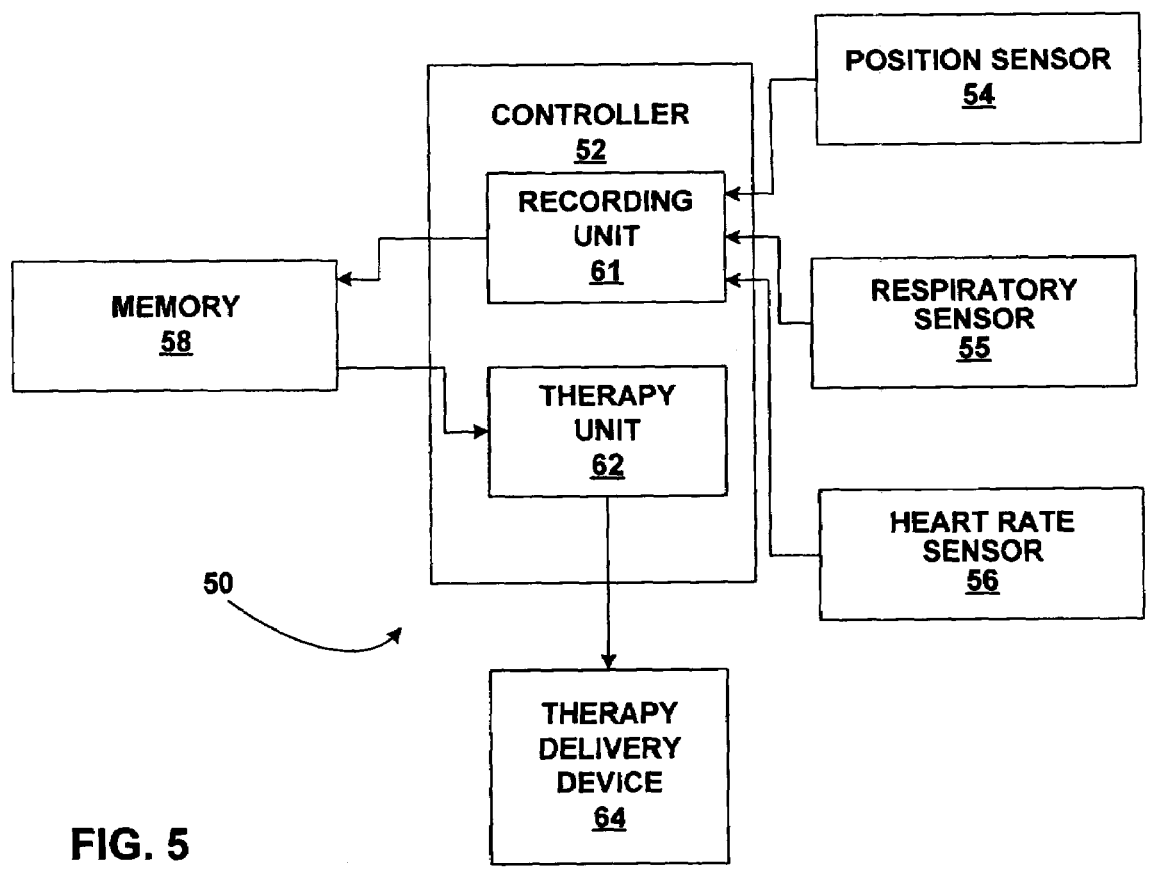
FIG. 5 is a block diagram of an IMD according to another embodiment of the invention.

In addition, in some cases, the recorded sensed information may be used directly by the IMD to control the delivery of therapy. FIG. 5 is a block diagram of an IMD 50 according to another embodiment of the invention. IMD 50 may correspond to IMD 10 of FIG. 1. IMD 50 includes a position sensor 54, a respiratory sensor 55 and a heart sensor 56. The sensors 54, 55, 56 are coupled to a controller 52. In particular, sensors 54, 55, 56 are coupled to recording unit 61 of controller 52. A memory 58 for storing information sensed by one or more of sensors 54, 55, 56 is also coupled to recording unit 61 of controller 52.

Recording unit 61 receives sensed information from position sensor 54, respiratory sensor 55 and heart sensor 56, and based on the information received from sensors 54, 55, 56, recording unit 61 identifies when a patient is going to sleep or waking up. For example, recording unit 61 of controller 52 may execute an algorithm to identify that a patient is going to sleep or waking up when specific conditions are sensed by one or more of sensors 54, 55, 56. Upon identifying that a patient is going to sleep, recording unit 61 stores sensed information in memory 58. Similarly, upon identifying that a patient is waking up, recording unit 61 stores sensed information in memory 58. In this manner, memory 58 stores the useful information accumulated during periods where the balance changes between the sympathetic and parasympathetic nervous systems.

In the example of FIG. 5, controller 52 also includes a therapy unit 62, which is coupled to a therapy delivery device 64. For example, therapy deliver device 64 may comprise a stimulation electrode for providing therapeutic stimulation to the patient, a drug delivery device for delivery of therapeutic agents to the patient, or any other device capable of delivering any type of therapy to the patient. In any case, therapy unit 62 uses the sensed information recorded in memory 58 to control therapy deliver device 64. In this manner, the recorded sensed information in memory 58 may be used directly by IMD 50 to control the delivery of therapy by therapy delivery device 64.

A number of embodiments of the invention have been described. However, one skilled in the art will appreciate that the invention can be practiced with embodiments other than those disclosed. For example, the invention may be used in any IMD that has sensing capabilities.

Example hardware implementations of controllers 25 or 55 include implementations within an application specific integrated circuit (ASIC), a field programmable gate array (FPGA), a programmable logic device, specifically designed hardware components, one or more processors, or any combination thereof. If implemented in software, a computer readable medium may store computer readable instructions, e.g., program code, that can be executed by a processor or DSP to carry out one of more of the techniques described above. For example, the computer readable medium may comprise memory 28 or 58, such as random access memory (RAM), read-only memory (ROM), non-volatile random access memory (NVRAM), electrically erasable programmable read-only memory (EEPROM), flash memory, or the like. The computer readable medium may comprise computer readable instructions that when executed in an IMD to carry out one or more of the techniques described herein. The disclosed embodiments are presented for purposes of illustration and not limitation, and the invention is limited only by the claims that follow.

What is claimed is:

1. An implantable medical device comprising:
   a first sensing unit configured to sense one or more physiological parameters;
   a second sensing unit configured to sense a first parameter indicative of a patient initiating a sleep state at a first time and a second parameter indicative of the patient having entered a state of being asleep at a second time;

a memory unit configured to store sensed data; and a controller operably coupled to the first sensing unit, the second sensing unit and the memory and configured to identify a first time interval between the first time and the second time and causes data sensed by the first sensing unit during the first time interval to be recorded in the memory unit, the data recording starting in response to sensing the first parameter and continuing for the first time interval, the data recording stopping in response to sensing the second parameter.

2. The implantable medical device of claim 1, wherein the first parameter is a signal triggered by the patient.

3. The implantable medical device of claim 1, wherein the first parameter includes a reduction in heart rate below a heart rate threshold.

4. The implantable medical device of claim 1, wherein the first parameter includes a reduction in a sensed respiratory rate below a respiratory rate threshold.

5. The implantable medical device of claim 1, wherein the first parameter includes an indication of positioning of the patient relative to the ground.

6. The implantable medical device of claim 1, wherein the second sensing unit is further configured to sense a third parameter indicative of a sleeping patient beginning to enter a waking state from an asleep state at a third time and a fourth parameter indicative of the patient being awake at a fourth time, wherein second time interval is defined between the third time and fourth time.

7. The implantable medical device of 6, wherein the third parameter includes an increase in the patient's heart rate above a heart rate threshold.

8. The implantable medical device of 6, wherein the third parameter includes an increase in the patient's respiratory rate above a respiratory rate threshold.

9. An implantable medical device comprising:
   a controller;
   a memory coupled to the controller;
   a heart sensor coupled to the controller;
   a respiratory sensor coupled to the controller; and
   a position sensor coupled to the controller, wherein the controller configured to identify a first sensed parameter indicative of a patient initiating a sleep state at a first time and a second sensed parameter indicative of the patient having entered a state of being asleep at a second time which defines a first time interval between the first time and the second time and the controller records in the memory information sensed by one or more of the sensors during the first time interval, the data recording starting in response to sensing the first parameter and continuing for the first time interval, the data recording stopping in response to sensing the second parameter.

10. The implantable medical device of claim 9, further comprising a telemetry unit coupled to the controller to receive a programmable value establishing the time interval associated with the patient going to sleep.

11. The implantable medical device of claim 9, wherein the first sensed parameter includes at least two of the following:
   a reduction in heart rate below a heart rate threshold;
   a reduction in respiratory rate below a respiratory rate threshold; and
   an indication that the patient is lying down based on positioning of the position sensor.

12. The implantable medical device of claim 9, wherein the controller identifies a third parameter indicative of the patient beginning to enter a waking state from a sleep state at a third time and a fourth parameter indicative of the patient being awake at a fourth time with a second time interval defined between the third time and the fourth time and records information sensed by one or more of the sensors in the memory during the second time interval.

13. The implantable medical device of claim 12, wherein the third parameter includes:
   identifying an increase in heart rate above a heart rate threshold; and
   identifying an increase in respiratory rate above a respiratory rate threshold.

14. The implantable medical device of claim 9, further comprising a therapy delivery device couple to the controller, wherein the controller controls delivery of therapy by the therapy delivery device based on the information sensed by one or more of the sensors and recorded in the memory for the defined by the first time interval.

* * * * *